(12) United States Patent
Kanoh et al.

(10) Patent No.: US 9,433,369 B2
(45) Date of Patent: Sep. 6, 2016

(54) EYEWEAR

(71) Applicant: JIN CO., LTD., Gunma (JP)

(72) Inventors: Shinichiro Kanoh, Miyagi (JP); Ryuta Kawashima, Miyagi (JP); Hitoshi Tanaka, Tokyo (JP)

(73) Assignee: JIN CO., LTD., Gunma (JP)

( * ) Notice: Subject to any disclaimer, the term of this patent is extended or adjusted under 35 U.S.C. 154(b) by 295 days.

(21) Appl. No.: 13/709,066

(22) Filed: Dec. 10, 2012

(65) Prior Publication Data

US 2013/0324881 A1 Dec. 5, 2013

(30) Foreign Application Priority Data

May 29, 2012 (JP) .................................. 2012-122349

(51) Int. Cl.
| | |
|---|---|
| *A61B 3/10* | (2006.01) |
| *A61B 5/0496* | (2006.01) |
| *G06F 3/01* | (2006.01) |
| *A61B 3/113* | (2006.01) |
| *G02C 5/12* | (2006.01) |
| *G02C 11/00* | (2006.01) |
| *A61B 5/00* | (2006.01) |

(52) U.S. Cl.
CPC ............... *A61B 5/0496* (2013.01); *A61B 3/10* (2013.01); *A61B 3/113* (2013.01); *A61B 5/6803* (2013.01); *A61B 5/6844* (2013.01); *G02C 5/12* (2013.01); *G02C 11/10* (2013.01); *G06F 3/013* (2013.01); *A61B 5/6819* (2013.01)

(58) Field of Classification Search
CPC ........ A61B 3/10; A61B 5/0496; G06F 3/013
USPC ......................................................... 324/647
See application file for complete search history.

(56) References Cited

U.S. PATENT DOCUMENTS

| | | | |
|---|---|---|---|
| 2,961,486 A * | 11/1960 | Marks | 348/42 |
| 5,360,971 A | 11/1994 | Kaufman et al. | |
| 2004/0070729 A1 | 4/2004 | Wiebe et al. | |
| 2006/0061544 A1 | 3/2006 | Min et al. | |
| 2007/0279365 A1* | 12/2007 | Kageyama | 345/100 |

(Continued)

FOREIGN PATENT DOCUMENTS

| | | |
|---|---|---|
| JP | 2004-254876 A | 9/2004 |
| JP | 2007-212501 A | 8/2007 |

(Continued)

OTHER PUBLICATIONS

European Search Report for Application No./Patent No. 12195244.4-2319 dated Jan. 30, 2013.

(Continued)

*Primary Examiner* — Thomas F Valone (57) ABSTRACT

A problem related to a known eyewear-type electro-oculogram measuring apparatus which detects the eye potential using a pair of electrodes positioned outside both the eyes of a user and a pair of electrodes respectively positioned above and below one eye is that the two pairs of electrodes have had an impact on the skins of users, and discomfort on them. Besides, the electrodes are not excellent in design. The present invention provides eyewear including: a frame; a pair of nose pads; and a first electrode and a second electrode respectively provided on the surface of the pair of nose pads, the first electrode and the second electrode detecting eye potential.

13 Claims, 10 Drawing Sheets

(56) References Cited

U.S. PATENT DOCUMENTS

| | | | |
|---|---|---|---|
| 2009/0002626 A1 | 1/2009 | Wakabayashi | |
| 2009/0054802 A1 | 2/2009 | Kuo et al. | |
| 2010/0191140 A1* | 7/2010 | Terada | A61B 5/04842 600/544 |
| 2011/0170065 A1 | 7/2011 | Sugio et al. | |
| 2011/0170067 A1 | 7/2011 | Sato et al. | |
| 2011/0178784 A1* | 7/2011 | Sato | A61B 5/0496 703/2 |

FOREIGN PATENT DOCUMENTS

| WO | WO 99/13682 A2 | 3/1999 |
|---|---|---|
| WO | WO 2008/057200 | 5/2008 |

OTHER PUBLICATIONS

Office Action issued for Korean Patent Application No. 10-2013-0005371, issued by the Korean Intellectual Property Office on Feb. 24, 2014.

Patent Examination Report No. 1, issued by the Australian Patent Office for Patent Application No. 2013200170 on May 14, 2013.

Extended European Search Report for European Patent Application No. 15162401.2, issued by the European Patent Office on Jul. 31, 2015.

Office Action issued for Chinese Patent Application No. 201210548772.X, issued by the Chinese Intellectual Property Office on Mar. 23, 2015.

* cited by examiner

EYEWEAR

The contents of the following Japanese patent application are incorporated herein by reference: No. 2012-122349 filed on May 29, 2012.

BACKGROUND

1. Technical Field

The present invention relates to eyewear.

2. Related Art

An eyewear-type electro-oculogram measuring apparatus is known which detects the eye potential using two pairs of electrodes positioned around the eye of a user, for example as described in Patent Document No. 1.

Patent Document 1: Japanese Patent Application Publication No. 2004-254876

However, the two pairs of electrodes have had an impact on the skins of users, and discomfort on them. Besides, the electrodes are not excellent in design.

SUMMARY

In order to solve the above problem, according to a first aspect related to the innovations herein, provided is eyewear including: a frame; a pair of nose pads; and a first electrode and a second electrode respectively provided on the surface of the pair of nose pads, the first electrode and the second electrode detecting eye potential.

The stated eyewear may further include a first electric wire and a second electric wire buried in the frame, and respectively electrically connected to the first electrode and the second electrode. The stated eyewear may further include a third electrode provided on the surface of a bridge of the frame and detecting eye potential. The stated eyewear may further include a third electric wire electrically connected to the third electrode and buried in the frame.

The stated eyewear may further include a transmitting section that transmits, to an external apparatus, an electro-oculogram signal representing the eye potential detected by the first electrode and the second electrode; and a power supply section that supplies power to the transmitting section. The stated eyewear may further include a processing section that processes the electro-oculogram signal, where the transmitting section transmits, to the external apparatus, the electro-oculogram signal having undergone processing by the processing section.

The summary clause does not necessarily describe all necessary features of the embodiments of the present invention. The present invention may also be a sub-combination of the features described above.

DESCRIPTION OF EXEMPLARY EMBODIMENTS

Hereinafter, some embodiments of the present invention will be described. The embodiments do not limit the invention according to the claims, and all the combinations of the features described in the embodiments are not necessarily essential to means provided by aspects of the invention. The following describes embodiments of the present invention using drawings, and portions that are identical or similar are given the same reference numerals. The drawings are schematic views, and may not accurately reflect the actual relation or ratio between the plane size and the thickness.

Figure 1:
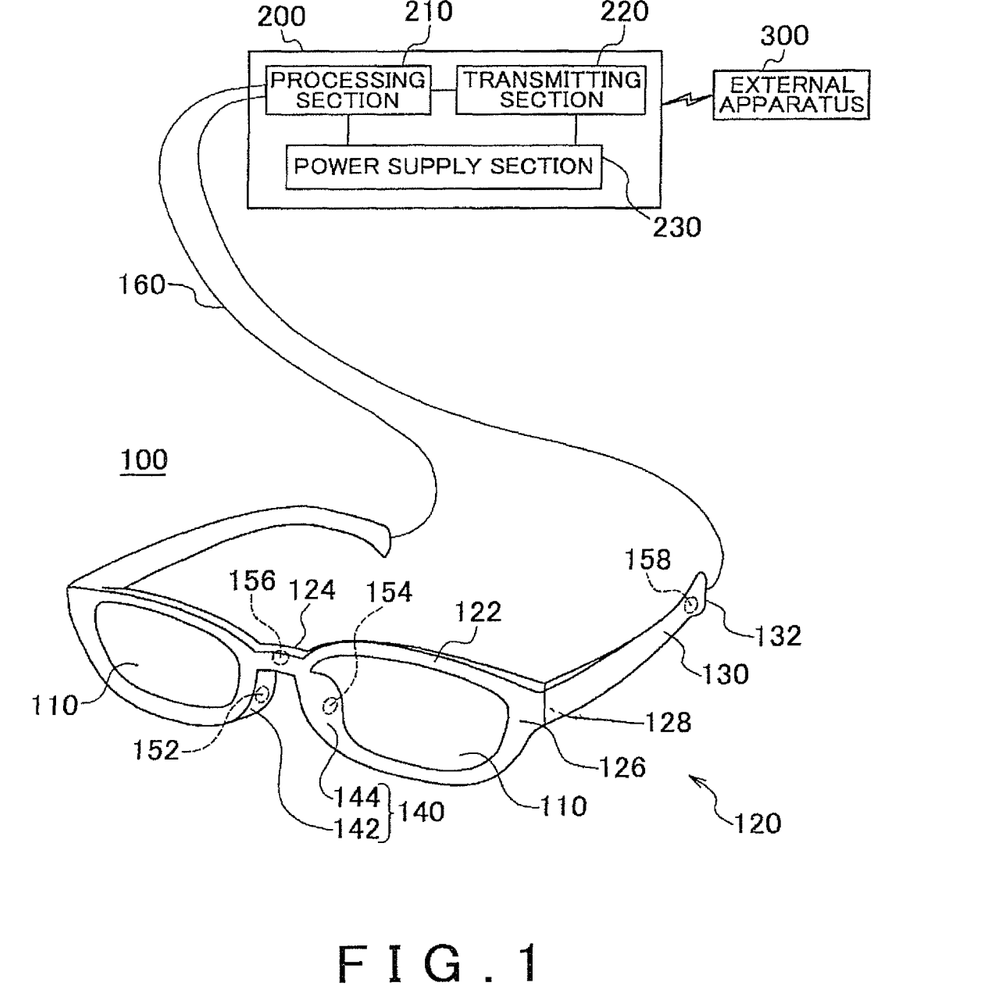
FIG. 1 schematically shows an example of a pair of glasses 100.

FIG. 1 schematically shows an example of a pair of glasses 100. The pair of glasses 100 includes a pair of lenses 110 and a frame 120. The pair of glasses 100 and the frame 120 may be an example of eyewear.

The frame 120 supports the pair of lenses 110. The frame 120 may include a rim 122, a bridge 124, an end piece 126, a hinge 128, a temple 130, an ear pad 132, a pair of nose pads 140, a first electrode 152, a second electrode 154, a third electrode 156, a ground electrode 158, and an electric wire 160. The pair of nose pads 140 include a right nose pad 142 and a left nose pad 144.

The rim 122, the end piece 126, the hinge 128, the temple 130, and the ear pad 132 are provided on the right side and the left side. The rim 122 supports the lens 110. The end piece 126 corresponds to the outer region of the rim 122, and the hinge 128 is used to support the temple 130 to be rotatable. The temples 130 press together the upper parts of the ears of a user. The ear pad 132 is provided at the tip of the temple 130. The ear pad 132 contacts the upper part of the ear of a user.

The first electrode 152 and the second electrode 154 are provided on respective surfaces of the pair of nose pads 140, to detect the eye potential. The first electrode 152 detects the eye potential of the right eye of a user. The second electrode 154 detects the eye potential of the left eye of a user. By providing an eye-potential-detecting electrode on a surface of the nose pad that inevitably contacts the skin of a user, the burden on the skin of a user can be alleviated, when compared to two pairs of electrodes which are made to contact the surrounding area of the eyes of a user.

The third electrode 156 is provided on a surface of the bridge 124, to detect the eye potential. The ground electrode 158 is provided on a surface of the ear pad 132. In this particular embodiment, the ground electrode 158 is provided on a surface of the left ear pad 132. The potential detected by the first electrode 152, the second electrode 154, and the third electrode 156 can be obtained relative to the potential detected by the ground electrode 158.

The pair of glasses 100 are connected to the electro-oculogram processing unit 200 via the electric wire 160. The electro-oculogram processing unit 200 may include a processing unit 210, a transmitting unit 220, and a power supply section 230. The first electrode 152, the second electrode 154, the third electrode 156, and the ground electrode 158 are connected to the processing section 210 via the electric wire 160.

The processing section 210 processes an electro-oculogram signal representing the eye potential detected by the first electrode 152 and the second electrode 154. In an example, the processing section 210 may process an electro-oculogram signal representing the potential of the first electrode 152 relative to the third electrode 156. The processing section 210 may also process an electro-oculogram signal representing the potential of the second electrode 154 relative to the third electrode 156. The processing of the electro-oculogram signal performed by the processing section 210 may include adding and subtracting processing by which the potential detected by the first electrode 152 and the potential detected by the second electrode 154 are adjusted. The processing of the electro-oculogram signal performed by the processing section 210 may include at least one of performing signal amplification or digital processing onto the electro-oculogram signal. The processing of the electro-oculogram signal performed by the processing section 210 may include transmitting the electro-oculogram signal representing the eye potential detected by the first electrode 152 and the second electrode 154 to the transmitting section 220 as it is.

The transmitting section 220 transmits the electro-oculogram signal having undergone the processing by the processing section 210, to an external apparatus 300. The transmitting section 220 may use wireless communication (e.g., Bluetooth (registered trademark), wireless LAN) or wired communication to transmit the electro-oculogram signal to the external apparatus 300. The power supply section 230 supplies power to the processing section 210 and the transmitting section 220.

The external apparatus 300 may be a computer terminal having a communication function. An exemplary external apparatus 300 is a mobile communication terminal (e.g., a portable phone, a smart phone) owned by a user. The external apparatus 300 may execute processing based on the electro-oculogram signal received from the transmitting section 220. For example, when having detected that the number of times of brinks of a user is increasing by referring to the received electro-oculogram signal, the external apparatus 300 may issue warning to prevent the user from falling asleep.

Figure 2:
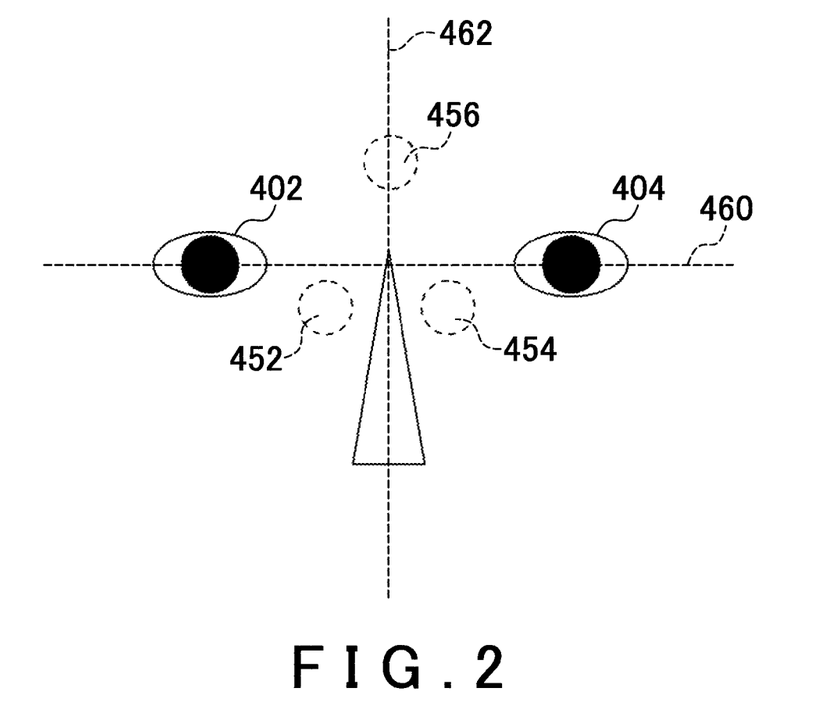
FIG. 2 schematically shows positions at which the electrodes make contact with a user.

FIG. 2 schematically shows positions at which the electrodes make contact with a user. A first contact position 452 represents the contact position of the first electrode 152. A second contact position 454 represents the contact position of the second electrode 154. A third contact position 456 represents the contact position of the third electrode 156. A horizontal center line 460 is defined as a center line in the horizontal direction connecting the center of the right eye 402 and the center of the left eye 404. A vertical center line 462 is defined as a center line that is orthogonal to the horizontal center line 460 and that passes through the center between the right eye 402 and the left eye 404 and.

The first contact position 452 and the second contact position 454 may desirably be positioned below the horizontal center line 460. The line connecting the center of the first contact position 452 and the center of the second contact position 454 may desirably be parallel to the horizontal center line 460. The distance between the first contact position 452 and the right eye 402 may desirably be equal to the distance between the second contact position 454 and the left eye 404. The first contact position 452 may desirably be distanced from the second contact position 454 by a certain length.

It is desirable that the third contact position 456 be positioned somewhere along the vertical center line 462. The third contact position 456 may desirably be in a position above the horizontal center line 460 and distanced from both of the first contact section 452 and the second contact section 454. In one example, the distance between the third contact position 456 and the right eye 402 may be set to be larger than the distance between the right eye 402 and the first contact position 452, and the distance between the third contact position 456 and the left eye 404 may be set to be larger than the distance between the left eye 404 and the second contact position 454.

In an eye ball, the corneal side has a positive charge and the retina side has a negative charge. Therefore, when a person looks up, the potential of the first electrode 152 obtained in relation to the third electrode 156 as well as the potential of the second electrode 154 obtained in relation to the third electrode 156 become negative. On the contrary, when a person looks down, the potential of the first electrode 152 obtained in relation to the third electrode 156 as well as the potential of the second electrode 154 obtained in relation to the third electrode 156 become positive. When a person looks to the right, the potential of the first electrode 152 obtained in relation to the third electrode 156 becomes negative, and the potential of the second electrode 154 obtained in relation to the third electrode 156 becomes positive. When a person looks to the left, the potential of the first electrode 152 obtained relative to the third electrode 156 becomes positive, and the potential of the second electrode 154 obtained in relation to the third electrode 156 becomes negative.

By detecting the potential of the first electrode 152 relative to the third electrode 156 as well as the potential of the second electrode 154 relative to the third electrode 156, the effect of noise can be effectively alleviated. The bridge 124 may be arranged at the upper end the rim 122 or in its vicinity, so as to distance the third contact position 456 from the first contact position 452 and the second contact position 454 as far as possible. The third electrode 156 may be provided above the center of the bridge 124. In such a case, it is desirable to adopt a bridge 124 that is wide in the vertical direction.

In stead of detecting the potential of the first electrode 152 relative to the third electrode 156, it is possible to subtract the potential of the third electrode 156 relative to the reference electrode, from the potential of the first electrode 152 relative to the reference electrode. Likewise, in stead of detecting the potential of the second electrode 154 relative to the third electrode 156, it is possible to subtract the potential of the third electrode 156 relative to the reference electrode, from the potential of the second electrode 154 relative to the reference electrode.

An example of the reference electrode is the ground electrode 158. In addition, another reference electrode may be provided in a position distanced from the first electrode 152, the second electrode 154, and the third electrode 156 of the pair of glasses 100. For example, a reference electrode may be provided on the right ear pad 132. The reference electrode may be provided at a position of the right temple 130 to be in contact with the skin of a user. The processing to subtract the potential of the third electrode 156 from the potential of the first electrode 152 relative to the reference electrode and the processing to subtract the potential of the third electrode 156 from the potential of the second electrode 154 relative to the reference electrode may be performed by the processing section 210 or by the external apparatus 300.

Figure 3:
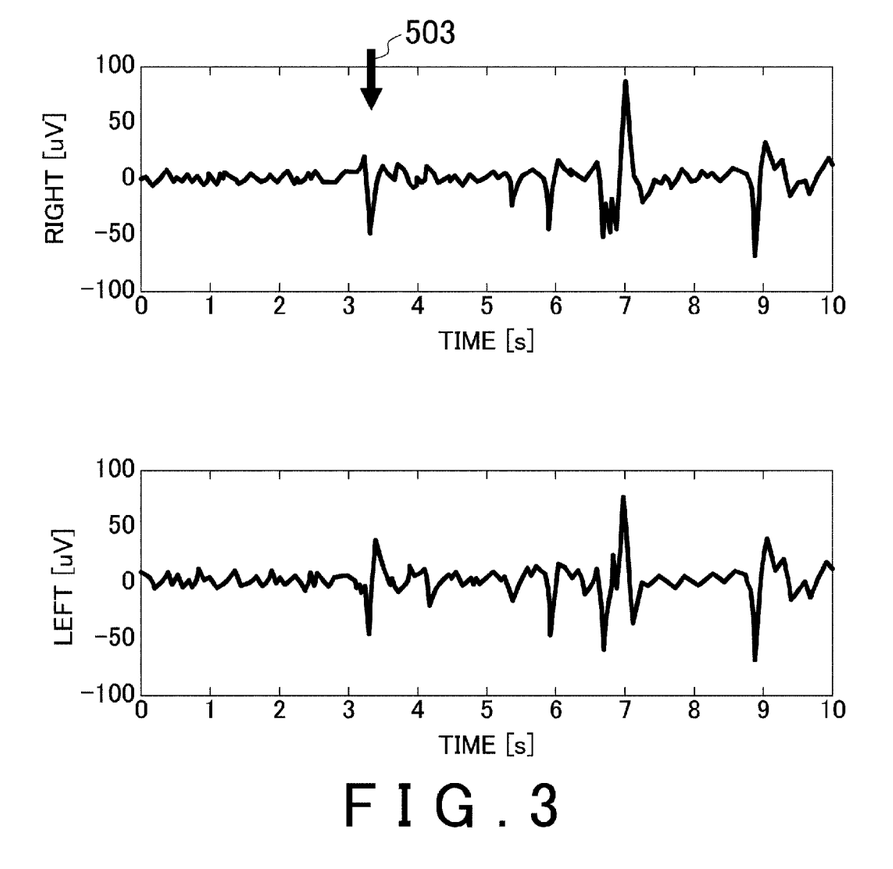
FIG. 3 schematically shows an exemplary electro-oculogram when the user looked down immediately after when he looked up.

FIG. 3 shows an exemplary electro-oculogram when the user looked down immediately after when he looked up. The upper electro-oculogram represents the electro-oculogram for the right eye showing the chronological change of the potential $V_1$ of the first electrode 152 relative to the third electrode 156. The lower electro-oculogram represents the electro-oculogram for the left eye showing the chronological change of the potential $V_2$ of the second electrode 154 relative to the third electrode 156. The longitudinal axis represents the voltage value. The lengthwise axis represents the time. The arrow 503 represents the timing at which the user looked up. At the timing shown by the arrow 503, both of the right-eye electro-oculogram and the left-eye electro-oculogram have a negative potential.

Figure 4:
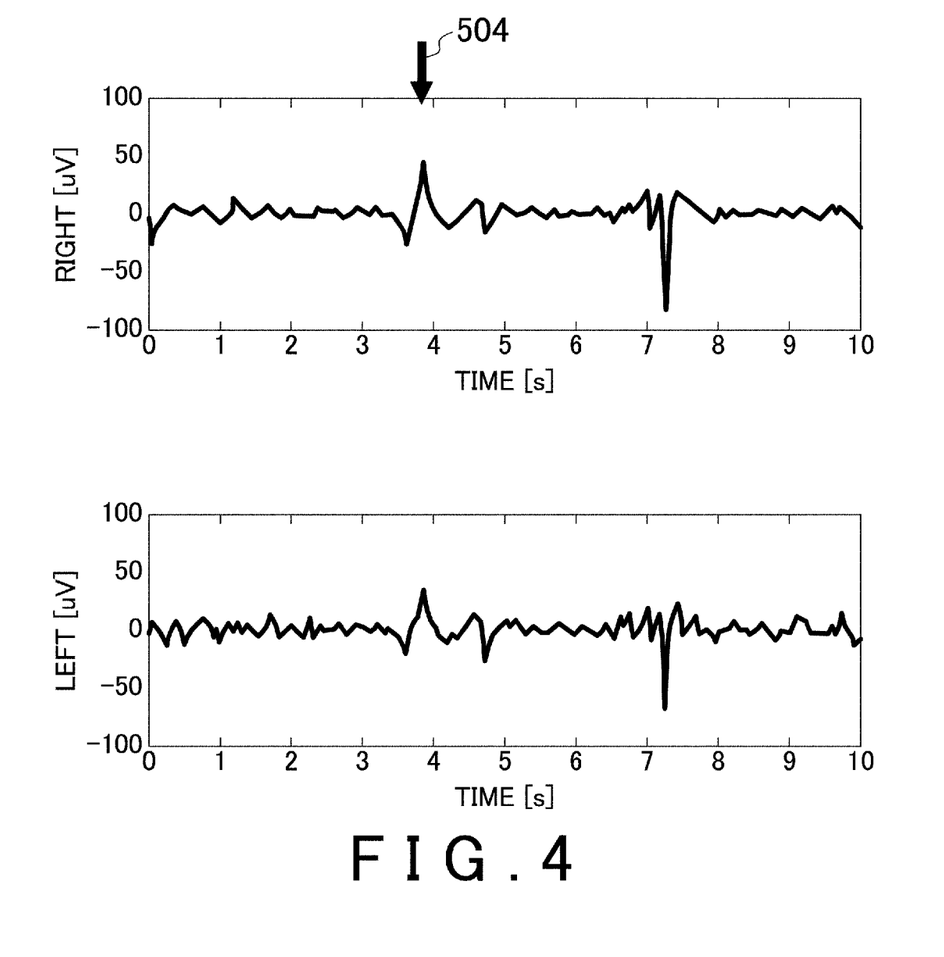
FIG. 4 schematically shows an exemplary electro-oculogram when the user looked up immediately after when he looked down.

FIG. 4 shows an exemplary electro-oculogram when the user looked up immediately after when he looked down. The arrow 504 represents the timing at which the user looked down. At the timing shown by the arrow 504, both of the right-eye electro-oculogram and the left-eye electro-oculogram have a positive potential.

Figure 5:
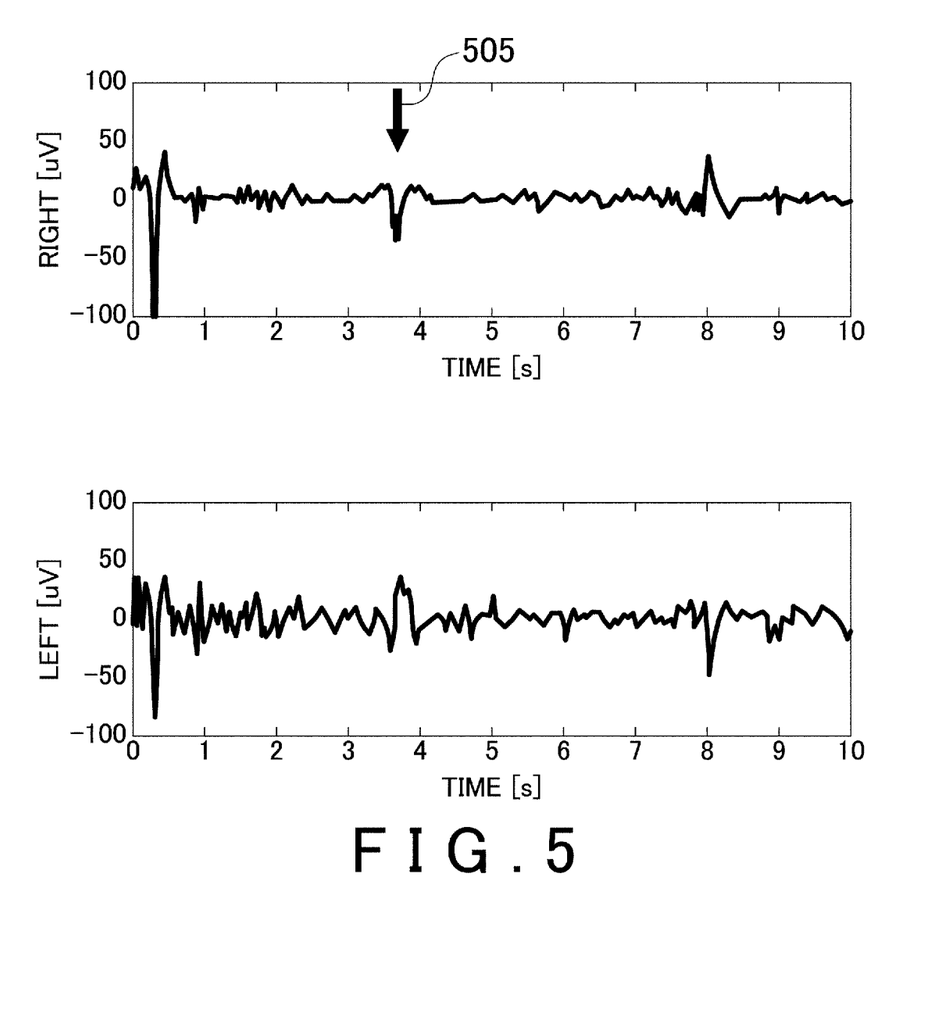
FIG. 5 schematically shows an exemplary electro-oculogram when the user looked in the left immediately after he looked right.

FIG. 5 shows an exemplary electro-oculogram when the user looked in the left direction immediately after he looked to the right. The arrow 505 represents the timing at which the user looked to the right. At the timing shown by the arrow 505, the right-eye electro-oculogram has a negative potential, and the left-eye electro-oculogram has a positive potential.

Figure 6:
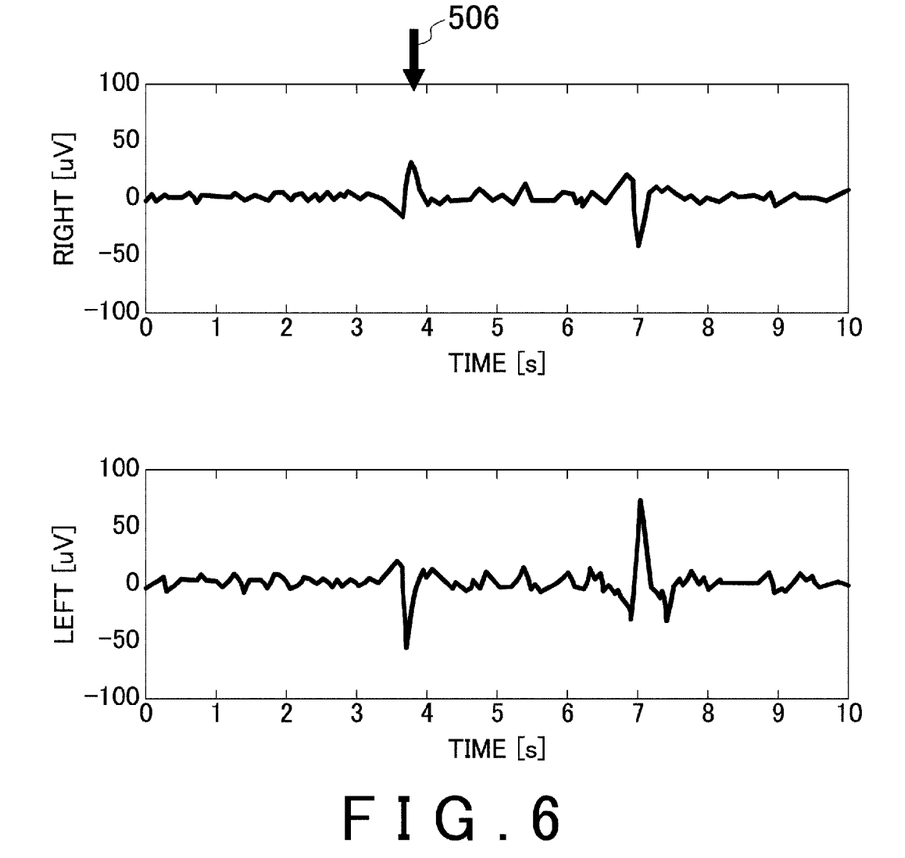
FIG. 6 schematically shows an exemplary electro-oculogram when the user looked in the right immediately after he looked left.

FIG. 6 shows an exemplary electro-oculogram when the user looked in the right immediately after he looked left. The arrow 506 represents the timing at which the user looked left. At the timing shown by the arrow 506, the right-eye electro-oculogram has a positive potential, and the left-eye electro-oculogram has a negative potential.

In this way, when the negative potential has been indicated in the right-eye electro-oculogram and the left-eye electro-oculogram, the user is identified to look up. When the positive potential has been indicated in the right-eye electro-oculogram and the left-eye electro-oculogram, the user is identified to look down. When the negative potential is indicated in the right-eye electro-oculogram and that the positive potential is indicated in the left-eye electro-oculogram, the user is identified to look right. When the positive potential is indicated in the right-eye electro-oculogram and that the negative potential is indicated in the left-eye electro-oculogram, the user is identified to look left.

It is further possible to enhance the detection accuracy of the visual line, by adding and subtracting the potential $V_1$ of the right-eye electro-oculogram and the potential $V_2$ of the left-eye electro-oculogram. For example when $V_1+V_2$ indicates a negative value and $V_1-V_2$ equals substantially zero, the user is identified to look up. When $V_1+V_2$ indicates a positive value and $V_1-V_2$ equals substantially zero, the user is identified to look down. When $V_1+V_2$ equals substantially zero and $V_1-V_2$ indicates a negative value, the user is identified to look to the right. When $V_1+V_2$ equals substantially zero and $V_1-V_2$ indicates a positive value, the user is identified to look to the left. By adding and subtracting the $V_1$ and $V_2$, the positive value and the negative value resulting after calculation will respectively become large. This means that the threshold value can be set large, and so misdetection to detect noise as visual line movement can be reduced.

Figure 7:
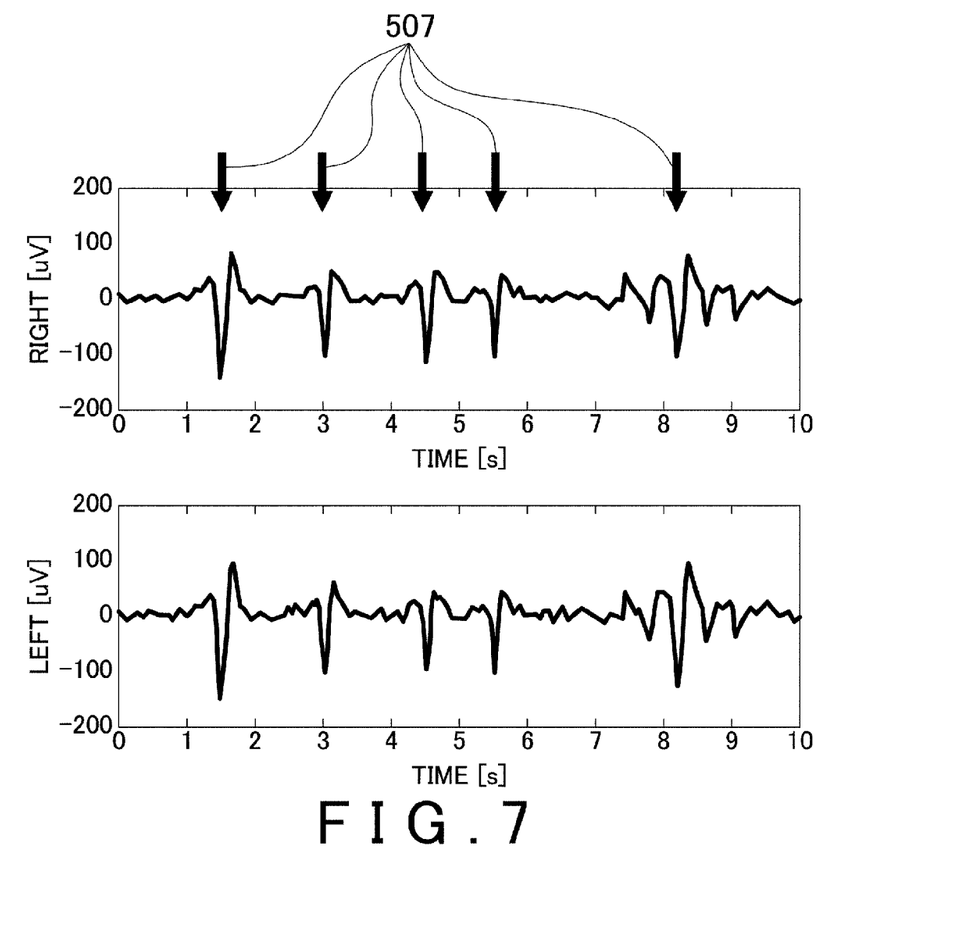
FIG. 7 schematically shows an exemplary electro-oculogram when he blinks.

FIG. 7 schematically shows an exemplary electro-oculogram when he blinks. The arrow 507 represents the timing at which the user has blinked. The processing section 210 and the external apparatus 300 may detect that the user has blinked, when having detected a sequence of pulses of approximately the same level of amplitude within a certain period of time in both of the right-eye electro-oculogram and the left-eye electro-oculogram. For example in FIG. 7, the user can be detected to have blinked when there occurred four consecutive pulses of −100 μV in 5 seconds.

Figure 8:
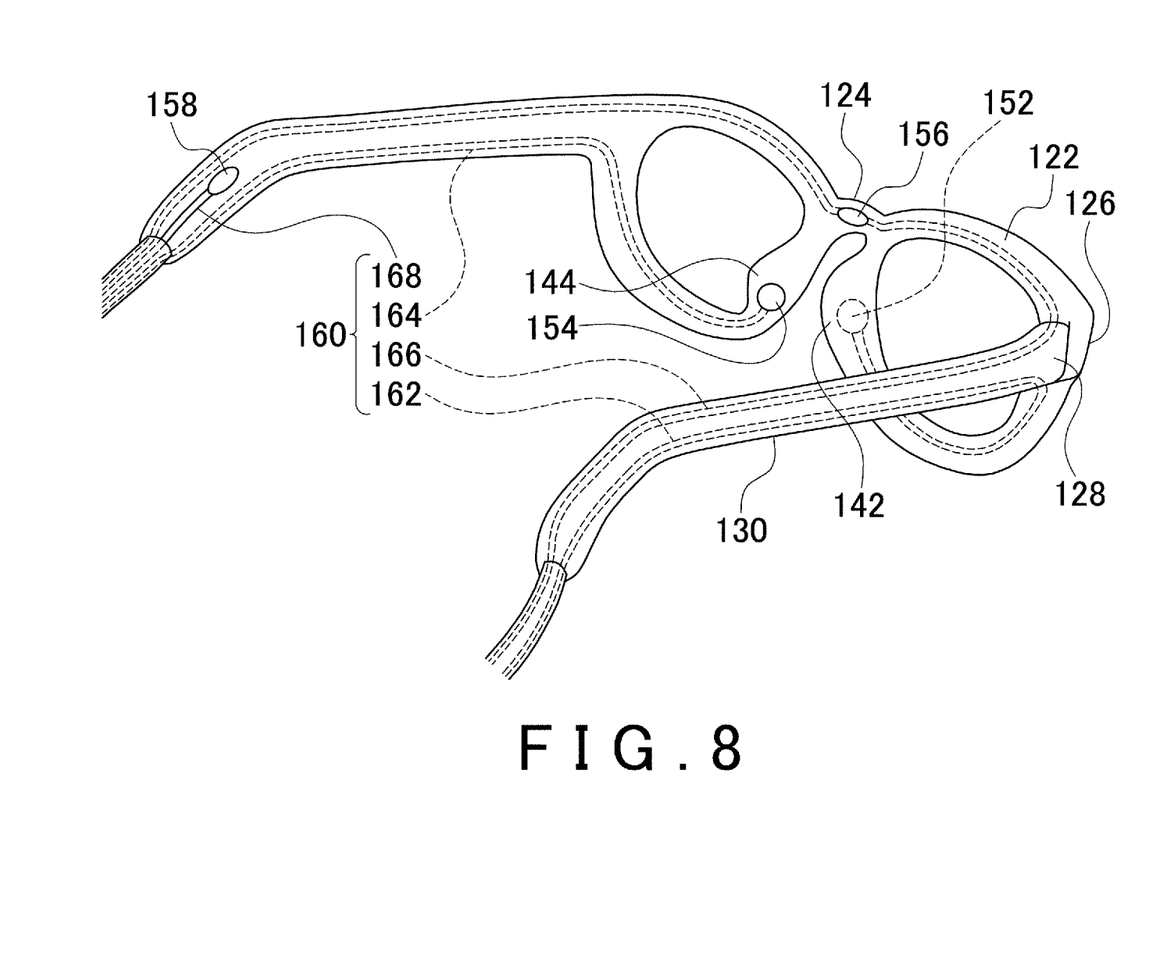
FIG. 8 schematically shows an example of the pair of glasses 100 viewed from the backside.

FIG. 8 schematically shows an example of the pair of glasses 100 viewed from the backside. The electric wire 160 may include a first electric wire 162, a second electric wire 164, a third electric wire 166, and a fourth electric wire 168. The first electric wire 162 may be electrically connected to the first electrode 152, and buried in the frame 120. The second electric wire 164 may be electrically connected to the second electrode 154, and buried in the frame 120. The third electric wire 166 may be electrically connected to the third electrode 156, and buried in the frame 120. The fourth electric wire 168 may be electrically connected to the ground electrode 158.

The first electric wire 162, the second electric wire 164, the third electric wire 166, and the fourth electric wire 168 may be an insulation electric wire. The shape of the insulation electric wire may be round or flat, and may even be a film wire. It is also possible to make the frame 120 from an insulator material, and the first electric wire 162, the second electric wire 164, and the third electric wire 166 from an uncoated conductive wire.

The first electric wire 162 passes the first electrode 152, the lower part of the right rim 122, the end piece 126, the hinge 128, the temple 130, and the ear pad 132, and then is exposed to outside. The second electric wire 164 passes the second electrode 154, the lower part of the left rim 122, the end piece 126, the hinge 128, the temple 130, and the ear pad 132 and then is exposed to outside. The third electric wire 166 passes the third electrode 156, the upper part of the right rim 122 and the left rim 122, the end piece 126, the hinge 128, the temple 130, and the ear pad 132, and then is exposed to outside. By burying the electric wires within the frame and not exposing them outside, the electric wires are prevented from being damaged. Moreover, the design of the pair of glasses 100 improves when compared to glasses having their electric wires exposed outside.

By burying the third electric wire 166 in both sides (left and right) of the frame 120, the pair of glasses 100 will have a well balanced weight on the right and left. Moreover, since the frame 120 has the same structure at the right and the left, the production process can be simpler than burying the third electric wire in the left or the right.

Alternatively, the third electric wire 166 can be buried in either the left or the right of the frame 120. In such a case, the amount of electric wire used can be reduced, to reduce the cost of the pair of glasses 100. When burying the third electric wire 166 in one side (i.e. the left or the right) of the frame 120, it should be desirable to burry the third electric wire 166 in the side which is opposite to the side in which the ground electrode 158 has been provided. By doing so, the number of electric wires that come out from the right ear pad 132 and the left ear pad 132 can be equaled.

As shown in FIG. 8, the first electrode 152 and the second electrode 154 can be provided below the center of the nose pad 140. By doing so, the first electrode 152 and the second electrode 154 can be prevented from being positioned right beside the user's eyes. If the first electrode 152 and the second electrode 154 are provided right beside the user's eyes, the visual line detection accuracy may be degraded because the potential detected will be similar between a case in which the user has looked up and a case in which the user has looked down. By providing the first electrode 152 and the second electrode 154 below the nose pad 140, the potential can be clearly differentiated between in a case in which the user has looked up and in a case in which the user has looked down, to prevent worsening of visual line detection accuracy.

Figure 9:
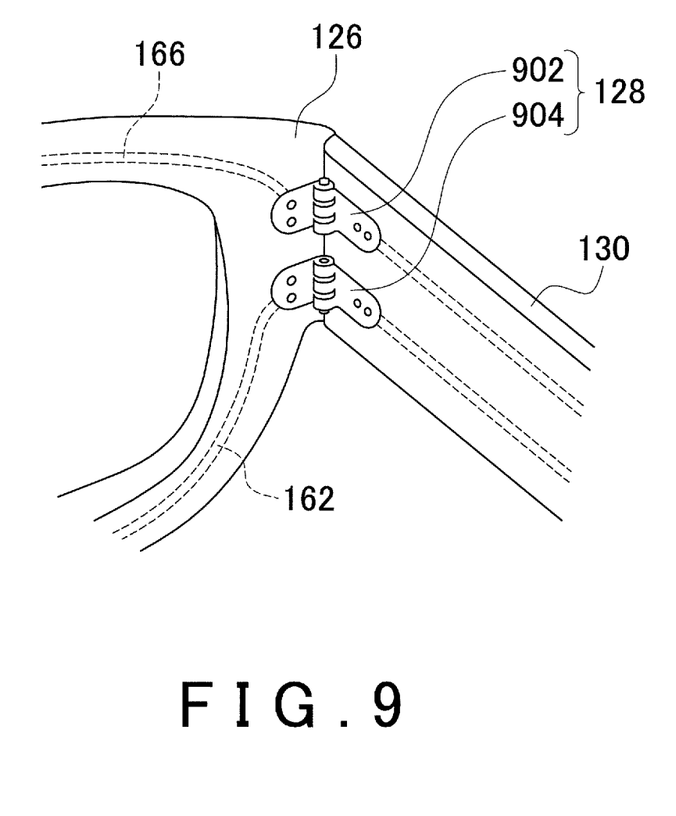
FIG. 9 schematically shows an example of a partially enlarged view of the pair of glasses 100 viewed from the backside.

FIG. 9 schematically shows an example of a partially enlarged view of the glasses 100 viewed from the backside. The hinge 128 may include a first hinge 902 and a second hinge 904. The first hinge 902 and the second hinge 904 may be made of an electrically conductive material. The first hinge 902 makes contact with the portion of the third electric wire 166 which is buried in the rim 122, and the portion of the third electric wire 166 which is buried in the temple 130. By doing so, the portion of the third electric wire 166 which is buried in the rim 122 can be in electrical conduction with the portion of the third electric wire 166 which is buried in the temple 130.

The second hinge 904 makes contact with the portion of the first electric wire 162 which is buried in the rim 122, and the portion of the first electric wire 162 which is buried in the temple 130. By doing so, the portion of the first electric wire 162 which is buried in the rim 122 can be in electrical conduction with the portion of the first electric wire 162 which is buried in the temple 130. The hinge 128 on the left side can also have the similar structure. By having two hinges distanced from each other, the first electric wire 162 can be electrically isolated from the third electric wire 166, as well as electrically isolating the second electric wire 164 from the third electric wire 166.

Figure 10:
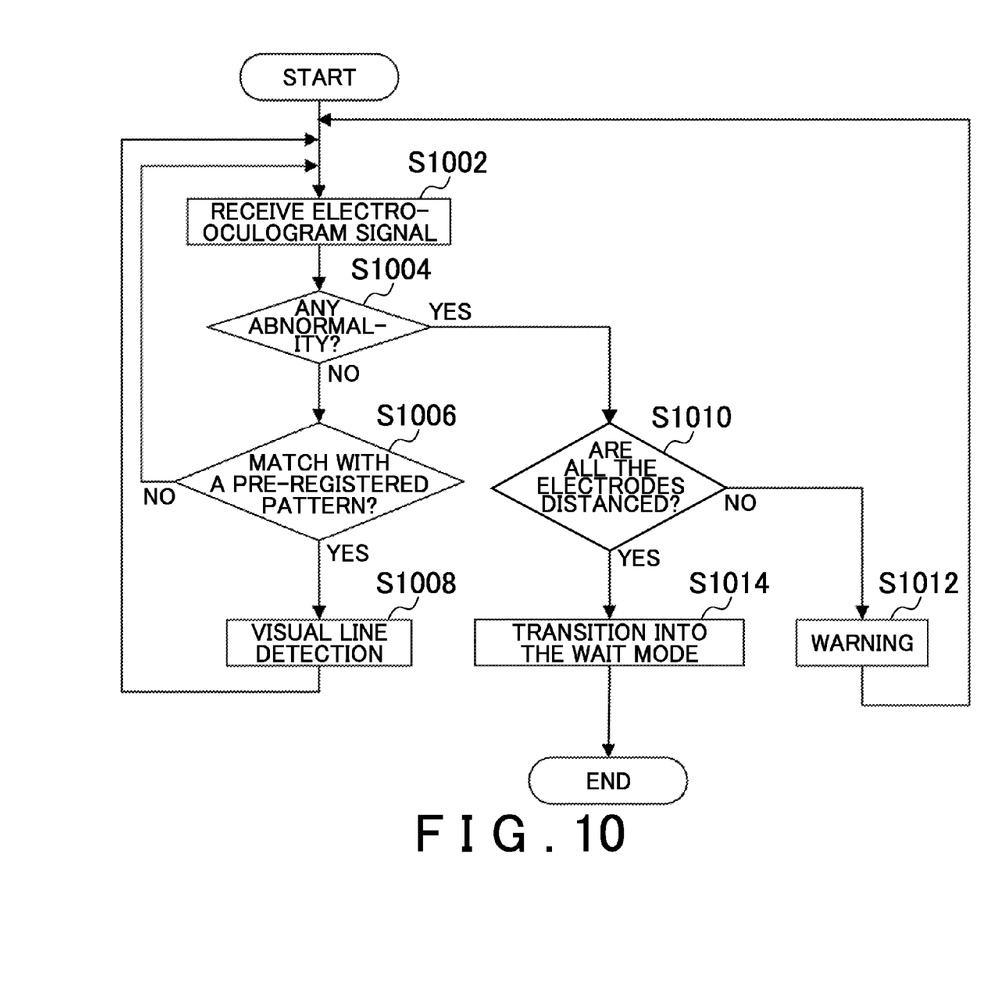
FIG. 10 shows a flowchart of a visual line detection processing performed by an external apparatus.

FIG. 10 shows a flowchart of a visual line detection processing performed by an external apparatus 300. The operation in the flow chart starts by bringing the first electrode 152, the second electrode 154, the third electrode 156, and the ground electrode 158 into contact with the skin of a user wearing the pair of glasses 100, and by moving into the operation mode in which the external apparatus 300 executes visual line detection processing.

In Step S1002, the external apparatus 300 receives an electro-oculogram signal from the transmitting section 220. The following explains the operation, by taking an example in which the potential detected by each electrode is received as it is.

In Step S1004, the external apparatus 300 determines whether there is abnormality in the received electro-oculogram signal. The external apparatus 300 will determine abnormality, when at least one of the first electrode 152, the second electrode 154, and the third electrode 156 has detected the potential of zero for a certain period of time or longer. For example, the external apparatus 300 determines that there is abnormality when at least one of the first electrode 152, the second electrode 154, and the third electrode 156 has detected the potential that exceeds a predetermined threshold value. When there is no abnormality found in Step S1004, the control proceeds to Step S1006.

In Step S1006, the external apparatus 300 determines whether the potential detected by the first electrode 152 relative to the third electrode 156 and the potential detected by the second electrode 154 relative to the third electrode 156 match a pre-registered pattern. An example of the pre-registered pattern may be as shown in FIG. 3 through FIG. 7. When there is determined a match with any of the pre-registered patterns in Step S1006, the control proceeds to Step S1008, and when there is not determined any match, the control returns to Step S1002.

In Step S1008, the external apparatus 300 determines the visual line of the user. The external apparatus 300 determines that the user is looking up, when the pre-registered pattern that has matched in Step S1006 has matched to the pattern shown in FIG. 3. The external apparatus 300 may execute the processing corresponding to the determined visual line. After having determined the visual line in Step S1008, the control returns to Step S1002.

When abnormality is found in Step S1004, the control proceeds to Step S1010. In Step S1010, the external apparatus 300 determines whether the abnormality indicates distancing away of all the electrodes. In other words, it is determined whether all the first electrodes 152, the second electrode 154, the third electrode 156 are distanced away from the skin of a user. The external apparatus 300 may determine that all the electrodes are distanced away when all the potential detected by the first electrode 152, the second electrode 154, and the third electrode 156 are zero for a certain period of time or longer.

In Step S1010, when it is determined that not all the electrodes are distanced, the control proceeds to Step S1012. In Step S1012, the external apparatus 300 warns the user. For example, when any one of the first electrode 152, the second electrode 154, and the third electrode 156 is distanced, the external apparatus 300 issues warning to notify the user of the existence of the distanced electrode(s). By warning the user, the user can be urged to adjust the position of the pair of glasses 100 to keep the electrodes in contact with him.

In Step S1010, when it is determined that all the electrodes are distanced away, the control proceeds to Step S1014. When all the electrodes are distanced away, it means that the pair of glasses 100 is removed from the user. Therefore in Step S1014, the external apparatus 300 moves onto the wait mode in which the external apparatus 300 waits before executing the next visual line detection processing. This ends the current visual line detection processing of the external apparatus 300. When the external apparatus 300 executes the visual line detection processing as described above, the visual line of the user can be detected. For example, when a part of the electrodes is distanced due to displacement of the pair of glasses 100 from the face of the user, the user can be notified and urged to adjust the position of the pair of glasses 100.

In the present embodiment, the pair of glasses is used as an example of eyewear. However, the eyewear is not limited to a pair of glasses. The eyewear can be anything that a user can wear, and may include glasses, sunglasses, goggles, a head mount display, and anything that can wear on the face or on the head.

In the present embodiment, the pair of glasses 100 includes the third electrode 156 and the third electric wire 166. However, the pair of glasses 100 is not necessarily limited to this configuration. A configuration is also possible in which the pair of glasses 100 does not include any of the third electrode 156 and the third electric wire 166. In such a configuration, the electro-oculogram showing the potential of the first electrode 152 relative to the reference electrode and the electro-oculogram showing the second electrode 154 relative to the reference electrode may be transmitted to the eternal apparatus 300. Here, the ground electrode 158 may be provided in the position of the third electrode 156 to use it as the reference electrode. Also, the ground electrode 158 provided on the left ear pad may be used as the reference electrode, or an additional electrode provided in a position distanced from the first electrode 152 and the second electrode 154 may be used as the reference electrode.

The electro-oculogram shown by the potential of the first electrode 152 relative to the reference electrode and the electro-oculogram shown by the potential of the second electrode 154 relative to the reference electrode have the characteristics similar to the characteristics of the electro-oculogram shown in FIG. 3-FIG. 6. The electro-oculogram shown by the potential of the first electrode 152 relative to the reference electrode and the electro-oculogram shown by the potential of the second electrode 154 relative to the reference electrode enable the external apparatus 300 to determine the visual line of a user. In this way, a configuration of not providing any of the third electrode 156 and the third electric wire 166 realizes an advantageous effect of reducing the number of electrodes and electric wires, which leads to reducing the weight and the cost of the pair of glasses 100.

The present embodiment has dealt with a pair of glasses 100 which has its nose pad 140 integrated with the rim 122. However, the pair of glasses 100 is not limited to this configuration. The pair of glasses 100 may include clings provided for the rim 122 and the nose pad 140 attached to the clings. In this case, the electrode provided on the surface of the nose pad 140 is electrically connected through the clings to the electric wire buried in the frame.

In the present embodiment, the pair of glasses 100 includes the first electric wire 162, the second electric wire 164, and the third electric wire 166 buried in the frame 120. However, the pair of glasses 100 is not limited to this configuration. The pair of glasses 100 includes the first electric wire 162, the second electric wire 164, and the third electric wire 166 provided along the surface of the frame 120.

The present embodiment has dealt with a case in which the first electrode 152 and the second electrode 154 are provided below the center of the nose pad 140. However, the present invention is not limited to this configuration. For example, the nose pad 140 can have an elongated section that elongates downward and that is provided with the first electrode 152 and the second electrode 154. By adopting this configuration, the first electrode 152 and the second electrode 154 can be brought in contact to the skin below the eyes of a user, even if the user has such a face configuration that the nose pad inevitably comes right beside his eyes.

The present embodiment has the third electrode 156 provided on the surface of the bridge 124. However, the present embodiment is not limited to this configuration. It is also possible to provide the bridge 124 with an elongated section that elongates upward, and to provide this elongated section with the third electrode 156. It is further possible to provide a movable section between the elongated section and the bridge 124, and move the elongated section up and down using this movable section for adjusting the position of the third electrode 156. By adopting this configuration, the contact position of the third electrode 156 can be adjusted to be away from the eyes, even if the user has such a face configuration that the third electrode 156 inevitably comes close to his eyes when wearing the pair of glasses.

The present embodiment has dealt with a case in which the first electric wire 162, the second electric wire 164, and the third electric wire 166 are exposed outside the ear pad 132. However, the present invention is not limited to this configuration. The first electric wire 162, the second electric wire 164, and the third electric wire 166 may extend from other portions. For example, the first electric wire 162, the second electric wire 164, and the third electric wire 166 can extend from the temple 130 or the end piece 126.

The present embodiment has taken an example that the external apparatus 300 is a mobile communication terminal such as a portable phone, a smart phone, or the like that is a separate body from the electro-oculogram processing unit 200. However, the present invention is not limited to this configuration. The external apparatus 300 may be provided as one piece with the electro-oculogram processing unit 200. In addition, although the electro-oculogram processing unit 200 was explained to be connected by the electric wire 160 to the pair of glasses 100 distanced apart from the electro-oculogram processing unit 200 in the present embodiment, the present invention is not limited to this configuration. In fact, the electro-oculogram processing unit 200 may be attached to the frame 120.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. Eyewear comprising:
   a frame;
   a pair of nose pads;
   a first electrode and a second electrode respectively provided on the surface of the pair of nose pads, the first electrode and the second electrode operable to detect eye potential;
   a third electrode provided equidistant from the first electrode and the second electrode on the surface of a bridge of the frame and operable to detect eye potential; and
   a computer programmed to determine whether a human wearing the eyewear has blinked on the basis of whether both a potential V1 of the first electrode relative to the third electrode and a potential V2 of the second electrode relative to the third electrode indicate a sequence of pulses of approximately the same level within a certain period of time.

2. The eyewear according to claim 1, wherein
   the first electrode is provided below the center of one of the nose pads, and the second electrode is provided below the center of the other of the pair of nose pads.

3. The eyewear according to claim 1, wherein
   the first electrode is provided on an elongated section of one of the nose pads, and the second electrode is provided on an elongated section of the other of the nose pads, and
   the elongated sections of each of the nose pads elongate downward such that the first electrode and the second electrode can be brought in contact to the skin below the eyes of a human wearing the eyewear.

4. The eyewear according to claim 1, further comprising:
a first electric wire, a second electric wire and a third electric wire respectively electrically connected to the first electrode, the second electrode and the third electrode and buried in the frame, wherein
the first electric wire is buried in the right side of the frame,
the second electric wire is buried in the left side of the frame, and
the third electric wire is buried in the both sides of the frame.

5. The eyewear according to claim 1, further comprising:
a first electric wire, a second electric wire and a third electric wire respectively electrically connected to the first electrode, the second electrode and the third electrode and buried in the frame; and
a ground electrode provided on a surface of either of a right ear pad or a left ear pad of the frame;
wherein the first electric wire is buried in the right side of the frame, the second electric wire is buried in the left side of the frame, and the third electric wire is buried in one of the right ear pad or the left ear pad of the frame in which no ground electrode is provided.

6. The eyewear according to claim 1, further comprising:
a first electric wire, a second electric wire and a third electric wire respectively electrically connected to the first electrode, the second electrode and the third electrode and buried in the frame;
wherein the first electric wire is buried in the right side of the frame, the second electric wire is buried in the left side of the frame, and the frame includes a right hinge and a left hinge both made of an electrically conductive material;
wherein the right hinge includes a first hinge and a second hinge that is provided below the first hinge and is distanced apart from the first hinge, and the left hinge includes a third hinge and a fourth hinge that is provided below the third hinge and is distanced apart from the third hinge; and
wherein at least one of the first hinge and the third hinge is in contact with the third electric wire, the second hinge is in contact with the first electric wire, and the fourth hinge is in contact with the second electric wire.

7. The eyewear according to claim 1, wherein
the frame includes a rim, and
the bridge is provided on an upper end of the rim.

8. The eyewear according to claim 1, wherein
the third electrode is provided above the center of the bridge.

9. The eyewear according to claim 1, wherein
the bridge includes an elongated section that elongates upward, and the elongated section is provided with the third electrode.

10. The eyewear according to claim 9, further comprising:
a movable section provided between the elongated section and the bridge, the movable section moving the elongated section up and down.

11. The eyewear according to claim 1, wherein
the computer is further programmed to check whether V1 and V2 satisfy pre-registered conditions including a first condition that V1+V2 indicates a negative value and V1−V2 equals substantially zero, a second condition that V1+V2 indicates a positive value and V1−V2 equals substantially zero, a third condition that V1+V2 equals substantially zero and V1−V2 indicates a negative value, and a fourth condition that V1+V2 equals substantially zero and V1−V2 indicates a positive value and to determine whether a human wearing the eyewear is looking up, down, to the right, or to the left on the basis of whether V1 and V2 satisfy the first condition, the second condition, the third condition, or the fourth condition.

12. A system comprising:
an eyewear including:
a frame,
a pair of nose pads,
a first electrode and a second electrode respectively provided on the surface of the pair of nose pads, the first electrode and the second electrode operable to detect eye potential, and
a third electrode provided equidistant from the first electrode and the second electrode on the surface of a bridge of the frame and operable to detect eye potential; and
a computer programmed to determine whether a human wearing the eyewear has blinked on the basis of whether both a potential V1 of the first electrode relative to the third electrode and a potential V2 of the second electrode relative to the third electrode indicate a sequence of pulses of approximately the same level within a certain period of time.

13. The system according to claim 11, wherein
the computer is further programmed to check whether V1 and V2 satisfy pre-registered conditions including a first condition that V1+V2 indicates a negative value and V1−V2 equals substantially zero, a second condition that V1+V2 indicates a positive value and V1−V2 equals substantially zero, a third condition that V1+V2 equals substantially zero and V1−V2 indicates a negative value, and a fourth condition that V1+V2 equals substantially zero and V1−V2 indicates a positive value and to determine whether a human wearing the eyewear is looking up, down, to the right, or to the left on the basis of whether V1 and V2 satisfy the first condition, the second condition, the third condition, or the fourth condition.

* * * * *